US008167891B2

(12) United States Patent
Terres et al.

(10) Patent No.: US 8,167,891 B2
(45) Date of Patent: May 1, 2012

(54) SYSTEM AND METHOD FOR FRACTURE REDUCTION

(75) Inventors: Jayson J. Terres, Tyler, TX (US);
Shaher A. Ahmad, Plano, TX (US);
Lisa R. Thornhill, Dallas, TX (US);
Solon B. Miles, III, Plano, TX (US);
Viorel Mocanu, Lewisville, TX (US)

(73) Assignee: OsteoMed LLC, Addison, TX (US)

( * ) Notice: Subject to any disclaimer, the term of this patent is extended or adjusted under 35 U.S.C. 154(b) by 949 days.

(21) Appl. No.: 12/176,677

(22) Filed: Jul. 21, 2008

(65) Prior Publication Data

US 2010/0016900 A1    Jan. 21, 2010

(51) Int. Cl.
*A61B 17/58* (2006.01)
*A61B 17/60* (2006.01)
*A61F 2/00* (2006.01)

(52) U.S. Cl. ........................................ 606/105; 606/282
(58) Field of Classification Search .......... 606/280–282, 606/105; 623/17.17–17.19
See application file for complete search history.

(56) References Cited

U.S. PATENT DOCUMENTS

| | | | |
|---|---|---|---|
| 6,764,489 B2 * | 7/2004 | Ferree | 606/279 |
| 2004/0097950 A1 | 5/2004 | Foley et al. | 606/96 |
| 2005/0277941 A1 | 12/2005 | Trumble et al. | 606/79 |

FOREIGN PATENT DOCUMENTS

WO    WO 96/05778    2/1996

OTHER PUBLICATIONS

Notification of Transmittal of the International Search Report and the Written Opinion of the International Searching Authority, or the Declaration; International Application No. PCT/ US2009/ 049345; International Filing Date Jul. 1, 2009, Mailed Oct. 15, 2009.

* cited by examiner

*Primary Examiner* — Thomas C. Barrett
*Assistant Examiner* — Andrew Yang
(74) *Attorney, Agent, or Firm* — Baker Botts L.L.P.

(57) ABSTRACT

A system for fracture reduction includes a reduction plate for reducing a fracture between a first bone segment and a second bone segment. The reduction plate includes, on a first side of the reduction plate, a travel slot and a screw hole. The travel slot is configured to slidably engage a first positioning element that extends into the first bone segment through the travel slot and the first screw hole is configured to affix the first side of the reduction plate to the first bone segment. The reduction plate includes, on a second side of the reduction plate, an adjustment hole and a second screw hole. The adjustment hole is configured to engage a second positioning element that extends into the second bone segment through the adjustment hole and the second screw hole is configured to affix the second side of the reduction plate to the second bone segment.

24 Claims, 6 Drawing Sheets

SYSTEM AND METHOD FOR FRACTURE REDUCTION

TECHNICAL FIELD

The present disclosure relates to a device for manipulating bones, and more particularly, the present disclosure relates to a system and method for fracture reduction.

BACKGROUND

When repairing a broken or fractured bone, a physician may often be faced with the task of reducing a fracture between two bone segments. More specifically, when reducing a fracture, a doctor may be required to properly align the first bone segment with the second bone segment and then secure the two segments together using, for example, plates, screws, wire, or other fastening means. Since the process of fracture reduction may often be a cumbersome undertaking, it would be beneficial to provide a system and method for efficiently reducing fractures.

SUMMARY

In particular embodiments, the present disclosure provides for a system and method for fracture reduction that includes a reduction plate for reducing a fracture between a first bone segment and a second bone segment. The reduction plate includes, on a first side of the reduction plate, a travel slot and a screw hole wherein the travel slot is configured to slidably engage a first positioning element that extends into the first bone segment through the travel slot and the first screw hole is configured to affix the first side of the reduction plate to the first bone segment via a first bone screw. The reduction plate also includes, on a second side of the reduction plate, an adjustment hole and a second screw hole wherein the adjustment hole is configured to engage a second positioning element that extends into the second bone segment through the adjustment hole and the second screw hole is configured to affix the second side of the reduction plate to the second bone segment via a second bone screw.

In particular embodiments, a system for fracture reduction further includes forceps having a first tip and a second tip respectively coupled to a first handle and a second handle via a hinge. The hinge includes a stop that limits a maximum separation distance between the first tip and the second tip wherein the maximum separation distance corresponds to a distance between a first end of the travel slot and an opposing end of the adjustment hole.

In particular embodiments, the first tip and the second tip respectively comprise the first positioning element and the second positioning element. Moreover, once the first tip is inserted into the first bone segment through the travel slot and the second tip is inserted into the second bone segment through the adjustment hole, the forceps are operable to adjust a width of the fracture while holding the first side of the reduction plate over the first bone segment and the second side of the reduction plate over the second bone segment.

In particular embodiments, the first positioning element and the second positioning element respectively include a first shoulder and a second shoulder. The first shoulder may be configured to rest on a first edge of the travel slot and the second shoulder may be configured to rest on a second edge of the adjustment hole. Moreover, a portion of the first positioning element disposed below the first shoulder may have a diameter that is less than a width of the travel slot and the first shoulder has a diameter that is greater than the width of the travel slot.

In particular embodiments, the first tip and the second tip are tapered such that the first tip is operable to capture the reduction plate by wedging into the travel slot and the second tip is operable to capture the reduction plate by wedging into the adjustment hole.

In particular embodiments, a first end of the first tip and a second end of the second tip are hooked inward such that the first end and the second end point toward one another. Furthermore, the first tip and the second tip may be bent at an angle such that the first tip and the second tip are angled up or down relative to a plane including the first handle and the second handle. Moreover, the forceps may comprise an adjustment mechanism operable to lockably adjust a separation distance between the first tip and the second tip.

In particular embodiments, the system for fracture reduction may include a first pin, a second pin, and forceps wherein the forceps may include a first clamp and a second clamp respectively coupled to a first handle and a second handle via a hinge wherein the forceps comprises a stop that limits a maximum separation distance between the first clamp and the second clamp, the maximum separation distance corresponding to a distance between a first end of the travel slot and an opposing end of the adjustment hole. Furthermore, the first positioning element may comprise the first pin and the second positioning element may comprise the second pin. The first clamp may be configured to rigidly engage the first pin the and the second clamp is configured to rigidly engage the second pin. Moreover, once the first pin and the second pin are inserted through the reduction plate respectively into the first bone segment and the second bone segment and the first clamp engages the first pin and the second clamp engages the second pin, the forceps are operable to adjust a width of the fracture while holding the first side of the reduction plate over the first bone segment and the second side of the reduction plate over the second bone segment.

Particular technical advantages of the present disclosure may be appreciated with reference to certain example aspects of a fracture reduction procedure that may be improved. To reduce a fracture between two bone segments in certain situations, a surgeon may use his hands or forceps or a combination of both to position the bone segments (e.g., to align the bone segments with one another). For example, to position a bone using forceps, a surgeon may use a bur to create a hole or anchor point in each of the bone segments for the forceps to bite into. The surgeon may then insert the forceps into the anchor points and may attempt to align the bone segments with one another using the forceps or his hands of a combination of both.

At the same time the surgeon is holding the fracture (e.g., the bone segments) in place with his hands, the forceps, or a combination of both, the surgeon may need to position and hold a reduction plate over the fracture, drill a pilot hole into each bone segment through one or more screw holes in the fracture reduction plate, and place a bone screw through the reduction plate on either side of the fracture line before the surgeon may let go of the bone segments lest the bone segments fall out of alignment before being affixed to the reduction plate.

In other situations, a surgeon may use k-wires or steiman pins in conjunction with his hands to reduce a fracture between two bone segments. For example, the surgeon may place the pins in the fractured bone segments and may use the pins to manipulate the bone segments in order to reduce the fracture. The surgeon may then be required to hold the bone segments in place with his hands, bone clamps, or some type of temporary fixation device, while positioning a fracture reduction plate over the fracture and drilling a pilot hole into each bone segment through one or more screw holes in the fracture reduction plate. Furthermore, the surgeon may then be required to place a bone screw through the reduction plate on either side of the fracture, all while holding the bone segments in alignment with one another. To achieve all of these steps in unison, a fracture reduction procedure may involve multiple surgeons.

Technical advantages of particular embodiments of the present disclosure may include providing a specially designed forceps and a specially designed reduction plate whereby a surgeon may use a single hand to align two bone segments with one another as well as hold a reduction plate in place over the fracture (e.g., a surgeon may use the forceps to hold both the bone and the reduction plate in place). Consequently, particular embodiments of the present disclosure may eliminate the need for multiple surgeons' hands to reduce a fracture. This technical advantage may be favorable in trauma situations that may occur in the middle of the night where only one surgeon may be available to operate.

Further technical advantages may include providing a system and method for fracture reduction whereby a surgeon may use a forceps to position the reduction plate relative to the bone segments thus allowing for a relatively small incision over the fracture site. Thus, particular embodiments of the present disclosure may decrease the chance of contaminating (e.g., introducing foreign bodies into) the incision site since the surgeon may not need to directly touch the bone segments with his fingers or hands in order to reduce the fracture or position the reduction plate. Particular embodiments of the present disclosure may provide for a reduced incision size and a reduced amount of dissection, thus leaving more of the vascular supply to the bone intact and promoting better healing, yet another technical advantage.

As an additional technical advantage of the present disclosure, a surgeon may use either the reduction plate or the forceps as a guide (e.g., a distance gauge) when drilling the fastening holes in the bone segments that may later be used by the forceps to couple the reduction plate to the bone segments. Thus, particular embodiments of the present disclosure may provide yet another technical advantage by eliminating any guess work on the part of the surgeon as to the appropriate placement of the fastening holes in the bone segments.

Other technical advantages of the present disclosure will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present disclosure and its advantages, reference is now made to the following descriptions, taken in conjunction with the accompanying drawings, in which.

DETAILED DESCRIPTION

Figure 1:
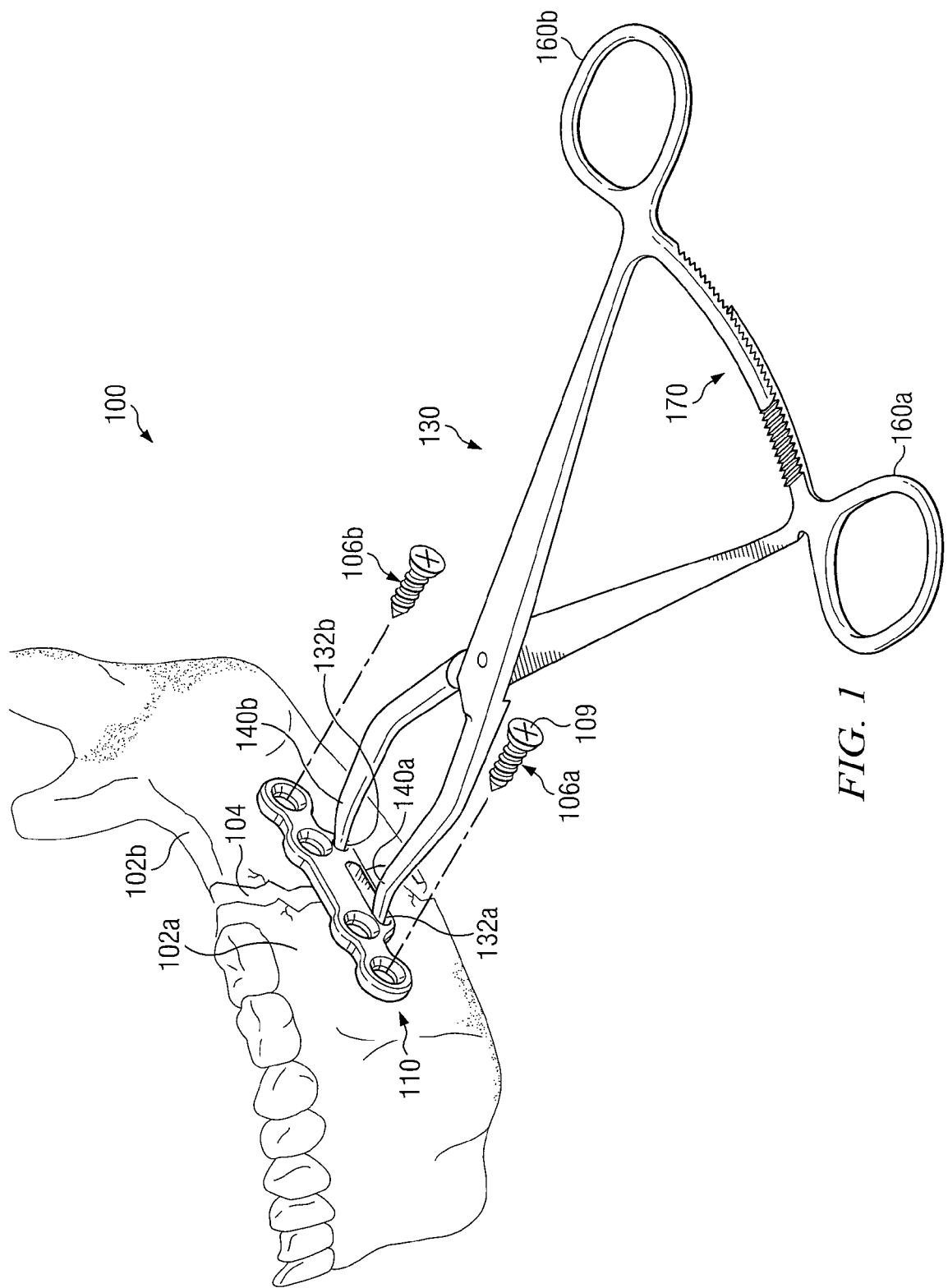
FIG. 1 illustrates an example system for fracture reduction that is being used to reduce a fracture that separates a first bone segment from a second bone segment.

FIG. 1 illustrates an example system 100 for fracture reduction that is being used to reduce a fracture 104 that separates a first bone segment 102a from a second bone segment 102b. Fracture 104 may be a complete or partial fracture of bone 102 meaning that bone segment 102a may be fully or partially separated from bone segment 102b by fracture 104. In the pictured embodiment, bone 102 is a mandible; however, particular embodiments of system 100 may be applied equally as well to reduce a fracture in virtually any bone in the body or to align and couple bone 102 to another bone or a synthetic element such as a surgical implant.

System 100 includes a forceps 130 and a reduction plate 110. In particular embodiments, forceps 130 may be used in conjunction with reduction plate 110 to align bone segment 102a with bone segment 102b while holding reduction plate 110 in place over fracture 104. More particularly, forceps 130 may hold a first side of reduction plate 110 ("side 110a") over bone segment 102a and a second side of reduction plate 110 ("side 110b") over bone segment 102b such that, once fracture 104 has been reduced using forceps 130, side 110a may be affixed to bone segment 102a and side 110b may be affixed to bone segment 102b using, for example, bone screws 106. After reduction plate 110 has been affixed to bone segments 102a and 102b, forceps 130 may be removed from bone 102 leaving fracture 104 to heal.

Forceps 130 may rigidly grapple into bone segment 102a and 102b in order to exert mechanical force on bone segment 102a relative to bone segment 102b (e.g., in order to squeeze bone segment 102a and 102b together across fracture 104). As an example and not by way of limitation, forceps 130 may grip bone segments 102a and 102b via specially designed tips 132 that are configured to extend into bone segments 102a and 102b through reduction plate 110. More particularly, tips 132 may grapple into predrilled fastening holes 105 (NOT PICTURED) in bone 102 through reduction plate 110 such that tips 132 contiguously engage reduction plate 110 and bone 102.

Forceps 130, and more specifically tips 132, may be used to align bone segment 102a with bone segment 102b by slidably engaging one or more portions of reduction plate 110. As an example and not by way of limitation, once tips 132 have been inserted into bone segments 102a and 102b through reduction plate 110, a physician or other party may use forceps 130 (e.g., may use a single hand on forceps 130) to align bone segment 102a with bone segment 102b via the slidable engagement between tips 132 and reduction plate 110 while at the same time holding reduction plate 110 in place across fracture 104.

In particular embodiments, as the physician aligns bone segment 102a with bone segment 102b (e.g., by squeezing the handles 160 of forceps 130 together), the position of bone segment 102a relative to 102b may be temporarily locked in place via an adjustment mechanism 170. Once bone segment 102a has been properly aligned with bone segment 102b, forceps 130 may hold all of the elements (e.g., bone segments 102a and 102b and reduction plate 110) in place via adjustment mechanism 170, leaving the physician free to affix reduction plate 110 to bone segments 102a and 102b using, for example, bone screws 106.

In particular embodiments, once fracture 104 has been reduced using forceps 130, a surgeon may use one or both of his hands to drill pilot holes in bone segments 102a and 102b and/or to insert bone screws 106 into bone segments 102a and 102b through reduction plate 110. In particular embodiments, forceps 130 may position reduction plate 110 relative to bone 102 as well as provide the ability to reduce fracture 104 through reduction plate 110 and hold both bone 102 and reduction plate 110 in place. One of ordinary skill in the art will appreciate that the above-described embodiments of system 100 were presented for the sake of explanatory simplicity and will further appreciate that the present disclosure contemplates any suitable coupling of forceps 130, reduction plate 110, and bone 102 whereby forceps 130 may be used to position bone segment 102a relative to bone segment 102b while simultaneously holding reduction plate 110 in place across fracture 104.

Figure 2:
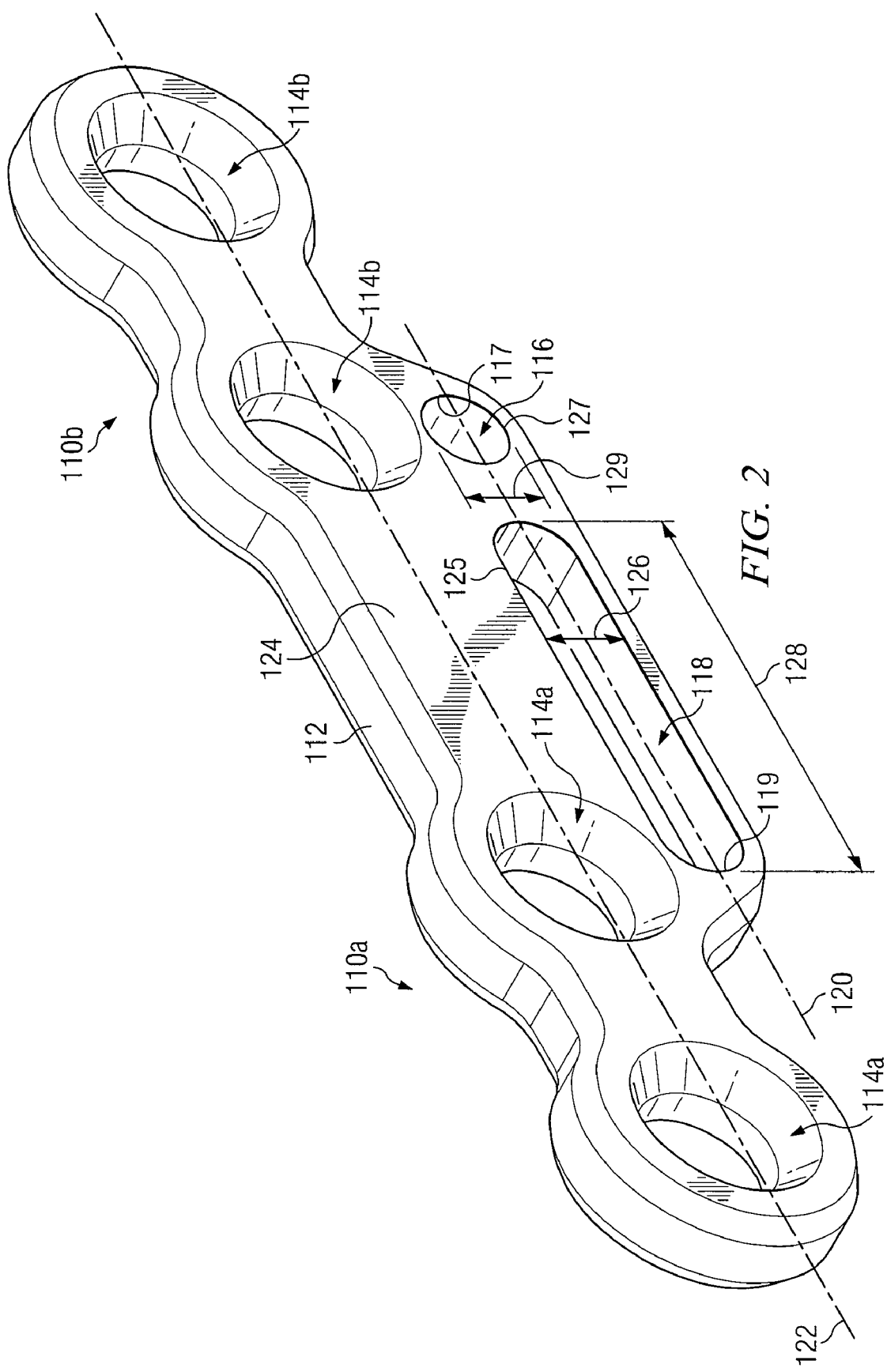
FIG. 2 illustrates an isometric view of an example embodiment of a reduction plate.

FIG. 2 illustrates an isometric view of an example embodiment of reduction plate 110. Reduction plate 110 includes a body 112 into which a plurality of screw holes 114, an anchor hole 116, and a travel slot 118 have been formed. Screw holes 114 reside along a first axis 122 of reduction plate 110 while anchor hole 116 and travel slot 118 reside along a second axis 122. For reference purposes, either or both of travel slot 118 and anchor hole 116 may be generically referred to as an adjustment hole. For reference purposes, reduction plate 110 may be referred to as having a first side 110a that is intended to be placed upon bone segment 102a and a second side 110b that is intended to be placed upon bone segment 102b. Though particular features of reduction plate 110 may be explained using such intended placement as a point of reference, this method of explanation is not meant to limit the scope of the present disclosure to any particular placement of plate 110 or any other components of system 100 relative to bone segments 102a and 102b or fracture 104.

Anchor hole 116 may be any opening in reduction plate 110 configured to rigidly engage one of tips 132. In particular embodiments anchor hole may correspond in size and shape (e.g., geometry) to a tip 132 of forceps 130 such that once tip 132 is inserted into anchor hole 116, the side of anchor hole 116 prevents tip 132 from moving relative to reduction plate 110. As an example and not by way of limitation, a diameter of anchor hole 116 may correspond to a diameter of tip 132 such that tip 132 fits snugly within anchor hole 116. As another example and not by way of limitation, anchor hole 116 may comprise one or more flat sides that engage one or more corresponding flat sides of tip 132 to prevent tip 132 from rotating in anchor hole 116. Anchor hole 116 may include an edge 127 upon which may abut a portion of tip 132 once tip 132 is inserted into anchor hole 116. In particular embodiments, once tip 132 is inserted into bone segment 102a or 102b through anchor hole 116, anchor hole 116 may act in conjunction with tip 132 to hold bone segment 102a or 102b immobile relative to reduction plate 110.

Travel slot 118 may be any opening in reduction plate 110 (e.g., an oblong channel) configured to provide slidable engagement between a tip 132 of forceps 130 and reduction plate 110 (e.g., providing a direction of travel along a length of reduction plate 110). In particular embodiments, a width 126 of travel slot 118 may correspond to a diameter of tip 132 such that, once tip 132 is inserted into travel slot 118, the side of travel slot 118 prevents tip 132a from tilting laterally within travel slot 118 (e.g., in the direction of the width 126 of travel slot 118) while allowing tip 132 to travel along a length 128 of travel slot 118. In particular embodiments, an edge 125 of travel slot 118 may be machined or beveled in order to facilitate slidable engagement with one of tips 132.

In particular embodiments, once tip 132 is inserted into bone segment 102a or 102b through travel slot 118, forceps 130 may be used to slidably position bone segment 102a or 102b along the length 128 of travel slot 118. As an example and not by way of limitation, if tip 132a is inserted into bone segment 102a through travel slot 118 and tip 132b is inserted into bone segment 102b through anchor hole 116, forceps 130 may be used to draw bone segment 102a toward bone segment 102b via the slidable engagement of tip 132a with travel slot 118.

Screw holes 114 may be any openings in reduction plate 110 configured to rigidly engage bone screws 106 such that a surgeon may rigidly affix reduction plate 110 to bone 102 by inserting bone screws 106 into bone 102 through screw holes 114. As an example and not by way of limitation, after positioning bone segment 102a relative to bone segment 102b using forceps 130, a physician may affix side 110a of reduction plate 110 to bone segment 102a by inserting bone screws 106 into bone segment 102a through screw holes 114a. Likewise, the physician may affix side 110b of reduction plate 110 to bone segment 102b by inserting bone screws 106 into bone segment 102b through screw holes 114b. In particular embodiments, each screw hole 114 may comprise a counter sink 120 (e.g., a conically recessed surface) whereby a top surface 109 of the heads of bone screws 106 may rest flush with a top surface 124 of reduction plate 110 once bone screws 106 have been inserted into bone 102 through reduction plate 110.

Reduction plate 110 may include any suitable number and configuration of screw holes 114, anchor holes 116, and/or travel slots 118 whereby forceps 130 may be used to adjust bone segment 102a relative to bone segment 102b while holding reduction plate 110 in place across fracture 104. As an example and not by way of limitation, travel slot 118 may be separated from anchor hole 116 by one or more of screw holes 114. As an additional example and not by way of limitation, travel slot 118, anchor hole 116, and screw holes 114 may reside along a same axis of reduction plate 110. As another example and not by way of limitation, reduction plate 110 may comprise two travel slots 118 each of which may slidably engage one of tips 132 thereby enabling forceps 130, once contiguously engaged with reduction plate 110 and bone 102, to adjust the position of bone segments 102a and 102b relative to reduction plate 110 and relative to each other. As yet another example and not by way of limitation, travel slot 118 and anchor hole 116 may reside along the first axis 120 of reduction plate 110 while each of screw holes 114 may reside along the second axis 122 of reduction plate 110. By positioning travel slot 118 and anchor hole 116 along a different axis of reduction plate 110 than the axis of screw holes 114, a surgeon may be provided with more working room around screw holes 114 with which to affix reduction plate 110 to bone 102 (e.g., travel slot 118 and anchor hole 116 may be located out of the way). One of ordinary skill in the art will appreciate that the above-described configurations of reduction plate 110 were presented for the sake of explanatory simplicity and will further appreciate that the present disclosure contemplates any suitable configuration and number of screw holes 114, anchor holes 116, and/or travel slots 118 in reduction plate 110 whereby forceps 130 may be used to position bone segment 102a relative to bone segment 102b while holding reduction plate 110 in place across fracture 104.

In particular embodiments, to use reduction plate 110, a surgeon may use one or more steps of the following example scenario. The surgeon may first bur a first fastening hole 105*a* into bone segment 102*a* and a second fastening hole 105*b* into bone segment 102*b*, either using plate 110 or a maximum separation distance between tips 132 as a guide by which to position fastening holes 105 in bone segments 102*a* and 102*b*. After creating fastening holes 105*a* and 105*b*, forceps 130 may by inserted into bone 102 through reduction plate 110 such that one of tips 132 grapples to bone segment 102*a* through anchor hole 116 and the other tip 132 grapples to bone segment 102*b* through travel slot 118. For example, each tip 132 may be inserted into either fastening hole 105*a* or 105*b* through either anchor hole 116 or travel slot 118.

After tips 132 have been inserted into bone segments 102*a* and 102*b* through reduction plate 110, forceps 130 may be closed using adjustment mechanism 170. As forceps 130 are closed, fracture 104 may be reduced and the position of reduction plate 110 may be locked in place over the fracture line of fracture 104 (e.g., by means of adjustment mechanism 170). Since forceps 130 may hold reduction plate 110 in place over fracture 104 while holding bone segments 102*a* and 102*b* together, the surgeon's hands may be freed up to drill pilot holes and place bone screws 106 on either side of fracture 104 through reduction plate 110. Once reduction plate 110 has been secured to bone 102 with at least one bone screw 106 on either side of fracture 104, forceps 130 may be removed and any remaining screw holes 114 may be pilot drilled and screwed to bone 102 with bone screws 106.

Figure 3:
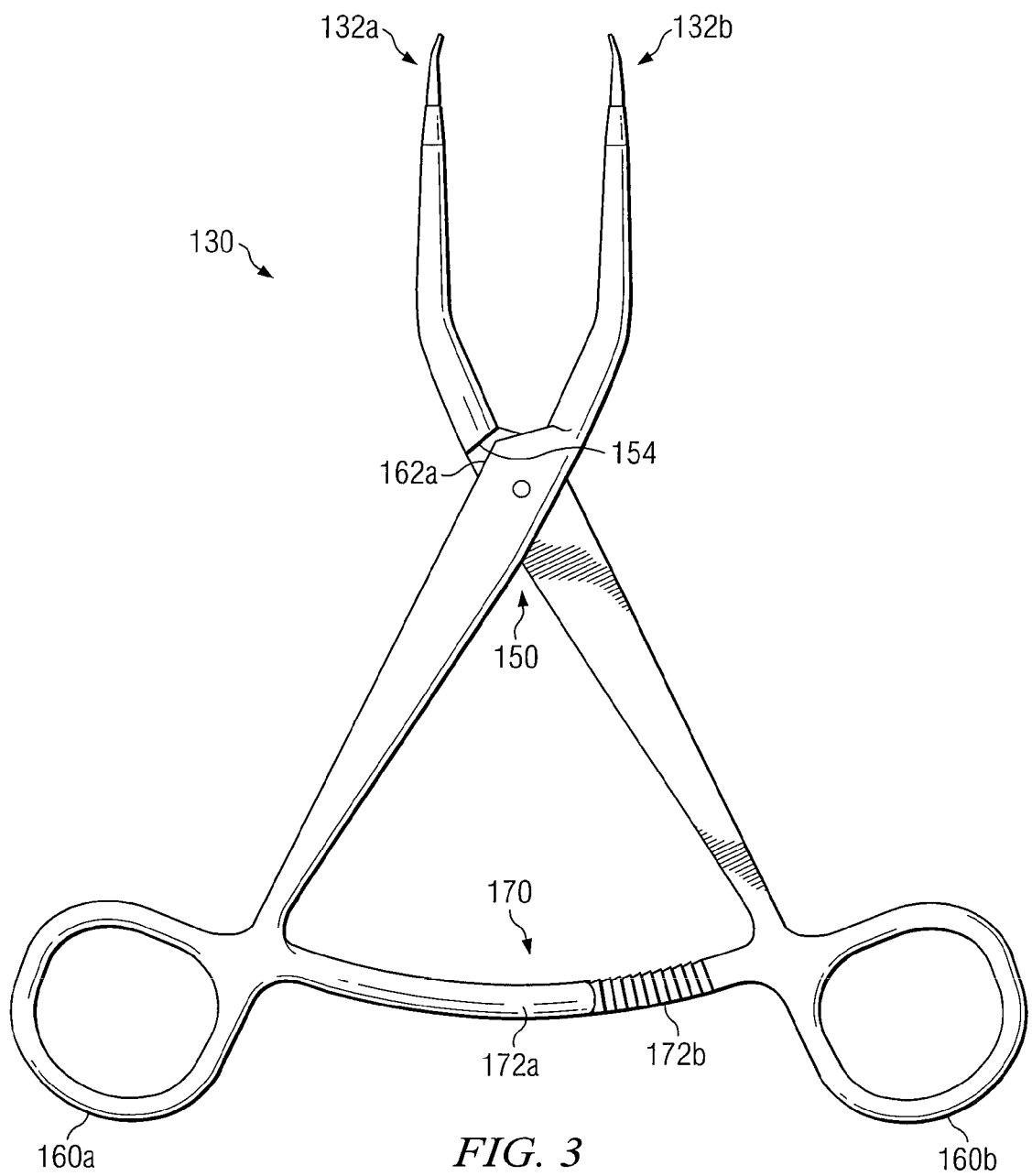
FIG. 3 illustrates an isometric view of example embodiment of a forceps.

FIG. 3 illustrates an isometric view of an example embodiment of forceps 130. Forceps 130*a* may be comprised of any rigid material or materials suitable for inclusion in a surgical instrument. As an example and not by way of limitation, forceps 130 may be comprised of stainless steel, titanium, or any other suitable metallic or non-metallic material. Forceps 130 includes a first handle 160*a* and a second handle 160*b* coupled to tips 132*a* and 132*b* through a hinge 150. Forceps 130 further includes an adjustment mechanism 170 disposed between handles 160*a* and 160*b* whereby handle 160*a* may be lockably positioned relative to handle 160*b*.

Adjustment mechanism 170 may be any mechanical fixture or device or combination of two or more such devices capable of lockably positioning handle 160*a* relative to handle 160*b*. As an example and not by way of limitation, adjustment mechanism 170 may comprise a ratchet mechanism whereby a plurality of notches and ridges disposed on a first arm 172*a* interlock with a plurality of notches and ridges disposed on a second arm 172*b* such that adjustment mechanism 170 prevents handle 160*a* from moving away from handle 160*b* unless adjustment mechanism 170 is unlocked (e.g., unless arm 172*a* is lifted from arm 172*b*). By lockably positioning handle 160*a* relative to handle 160*b*, adjustment mechanism 170 may be used to lockably position tip 132*a* relative to tip 132*b* through hinge 150 (e.g., adjustment mechanism 170 may be used to lockably position tip 132*a* relative to tip 132*b*).

Hinge 150 transmits mechanical force between handles 160 and tips 132 such that when handles 160 move toward one another, tips 132 move toward one another. Likewise, when handles 160 move away from one another, tips 132 move away from one another. In particular embodiments, a range of motion provided by hinge 150 may be limited by a stop 154. Stop 154 may be any mechanical device or fixture capable of limiting the range of motion provided by hinge 150. As an example and not by way of limitation, stop 154 may comprise a ridge of material on tip 132*a* disposed adjacent to hinge 150 and configured to abut an edge 162*a* of handle 160*a* once tips 132 are opened to a predetermined amount (e.g., a maximum separation distance). By limiting the range of motion provided by hinge 150, stop 154 may limit the maximum separation distance between tips 132.

In particular embodiments, the maximum separation distance between tips 132 may correspond to a distance between opposing ends of travel slot 118 and anchor hole 116. For example, stop 154 may prevent tips 132 from opening wider than the distance between the outermost ends of travel slot 118 and anchor hole 116 (e.g., end 117 of anchor hole 116 and end 119 of travel slot 118). Likewise, if reduction plate 110 comprises two travel slots 118, stop 154 may prevent tips 132 from opening wider than the distance between opposing ends (e.g., the outermost ends) of the two travel slots 118. By limiting the maximum separation distance between tips 132 to correspond with the distance between the outermost ends of travel slot 118 and anchor hole 116 (or between the outermost ends of two travel slots 118, if applicable), stop 154 enables a surgeon to use the tips 132 of forceps 130 as a guide (e.g., as a distance gauge) by which to create fastening holes 105*a* and 105*b* in bone segments 102*a* and 102*b*.

By using either forceps 130 or reduction plate 110 as a distance gauge for creating fastening holes 105*a* and 105*b*, the surgeon may later insert tips 132 into fastening holes 105*a* and 105*b* knowing that fastening holes 105*a* and 105*b* are properly spaced with respect to the adjustment holes (e.g., anchor hole 116 and/or travel slot(s) 118) in reduction plate 110. One of ordinary skill in the art will appreciate that the above-described embodiment of stop 154 was presented for the sake of explanatory simplicity and will further appreciate that the present disclosure contemplates any and all of configurations of and alterations to stop 154 capable of limiting the range of motion provided by hinge 150.

In particular embodiments, forceps 130 may be designed specifically for reduction plate 110. As an example and not by way of limitation, anchor hole 116 and travel slot 118 my be disposed within reduction plate 110. In particular embodiments, the tips 132 of forceps 130 may be specially designed to go through anchor hole 116 and travel slot 118 of reduction plate 110 and grapple to bone 102. In particular embodiments, forceps 130 may only open as wide as the distance between anchor hole 116 and the opposing end of the travel slot 118 thus eliminating any guess work on the part of a surgeon as to where he should use a bur to drill fastening holes 105*a* and 105*b* in bone segments 102*a* and 102*b*. In particular embodiments each tip 132 of forceps 130 may have a shoulder 134 (FIG. 4) to keep reduction plate 110 compressed against bone 102.

Figure 4:
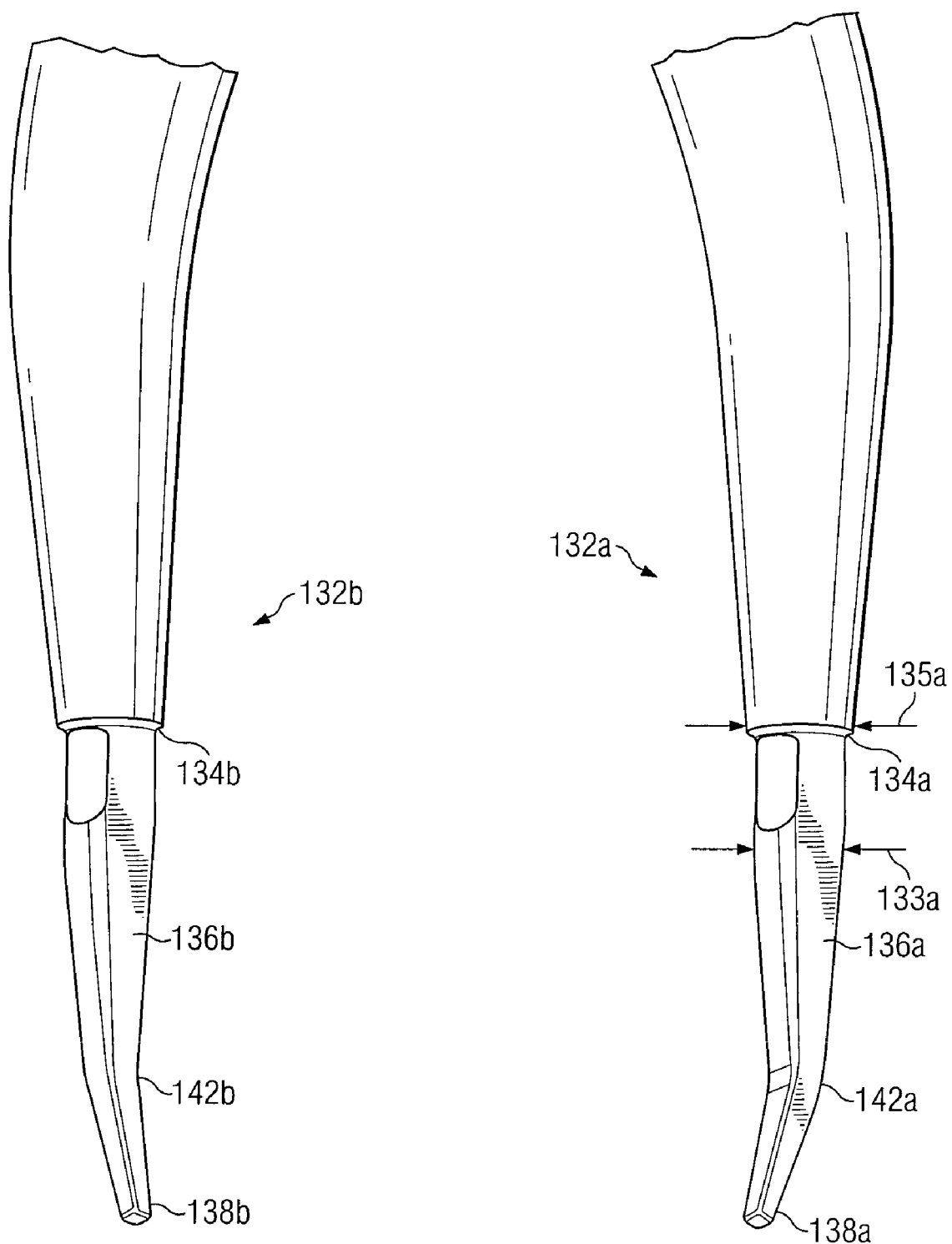
FIG. 4 illustrates an enlarged view of the tips of the forceps of FIG. 3.

FIG. 4 illustrates an enlarged view of tips 132. In particular embodiments, each tip 132 may include an end 138 that points slightly inward via a hook 142. Each tip 132 may further include one or more flattened sides 136 configured to fit snugly against the sides of travel slot 118 or within anchor hole 116 and a shoulder 134 configured to rest on the edge of travel slot 118 or anchor hole 116. Each tip 132 may also include a bend 140 (FIG. 1) disposed between ends 138 and handles 160 such that ends 138 angle up or down relative to handles 160 (e.g., upward or downward relative to the plane of handles 160).

In particular embodiments, each of ends 138 may be specially configured to bite into bone 102. As an example and not by way of limitation, each of end 138 may be sharpened (e.g., pointed) to aid tips 132 in grappling into bone 102. As another example and not by way of limitation, each of ends 138 may be hooked inward (e.g., may comprise a hook 142) to aid tips 132 in grappling into bone 102. Hook 142 may comprise a slight angle disposed above each of ends 138 such that ends 138 point slightly inward (e.g., toward one another). By angling ends 138 toward one another, hook 142 may enable ends 138 to poke into bone 102 when tips 132 are drawn together.

In particular embodiments, each of tips 132 may be geometrically configured to abut the edges of the adjustment holes (e.g., anchor hole 116 and/or travel slot(s) 118) in reduction plate 110 such that only a portion of each tip 132 may fit through the adjustment holes (e.g., anchor hole 116 and/or travel slot(s) 118) in reduction plate 110. As an example and not by way of limitation, each tip 132 or a portion thereof may be tapered (e.g., increasing in size as one moves from end 138 toward hinge 150) such that tip 132 may only partially extend through travel slot 118 or adjustment hole 116 before wedging into travel slot 118 or adjustment hole 116. Thus, the taper of each tip 132 may limit the portion of each tip 132 that may extend through the adjustment holes (e.g., anchor hole 116 and/or travel slot(s) 118) in reduction plate 110.

As an additional example and not by way of limitation, each tip 132 may include a shoulder 134 configured to rest on the edge of travel slot 118 or anchor hole 116 while the portion of tip 132 disposed below shoulder 134 may be configured to extend through travel slot 118 or anchor hole 116 into bone 102. For example, a diameter 133 of the portion of tip 132 disposed below shoulder 134 may be smaller in diameter than the width 126 of travel slot 118, while a diameter 135 of shoulder 134 may be greater in diameter than the width 126 of travel slot 118. Consequently, when tip 132 is inserted into travel slot 118, shoulder 134 may rest on (e.g., abut) the edge 125 of travel slot 118 while the portion of tip 132 disposed below shoulder 134 may extend through travel slot 118. As an additional example and not by way of limitation, a diameter 133 of the portion of tip 132 disposed below shoulder 134 may be smaller in diameter than the diameter of anchor hole 116, while a diameter 135 of shoulder 134 may be greater in diameter than the diameter of anchor hole 116. Consequently, when tip 132 is inserted into anchor hole 116, shoulder 134 may rest on (e.g., abut) the edge 127 of anchor hole 116 while the portion of tip 132 disposed below shoulder 134 may extend through anchor hole 116.

By configuring each tip 132 such that only a portion of each tip 132 may fit into either anchor hole 116 or travel slot 118, forceps 130 may be used to capture reduction plate 110 and to press reduction plate 110 firmly against the surface of bone 102 while reducing fracture 104.

In particular embodiments, each of tips 132 may include a bend 140 (FIG. 1) disposed between ends 138 and handles 160. Bend 140 may serve to angle ends 138 away from handles 160 (e.g., upward or downward relative to the plane of handles 160) such that once tips 132 are inserted into reduction plate 110, handles 160 do not reside directly above reduction plate 110, but rather are angled away from the top surface 124 of reduction plate 110. As an example and not by way of limitation, bend 140 may comprise a 40 degree angle relative to the plane of handles 160. Thus, when tips 132 are engaged with reduction plate 110, handles 160 may angle away from the top surface 124 of reduction plate 110 at an angle of approximately 40 degrees from perpendicular. By including bend 140 between ends 138 and handles 160, forceps 130 may provide a surgeon with more working room above the top surface 124 of reduction plate 110. One of ordinary skill in the art will appreciate that the above-described features of forceps 130 were described for the sake of explanatory simplicity and will further appreciate that the present disclosure contemplates the inclusion or exclusion of any such features or modifications thereto in order to enable forceps 130 to align and lock bone segment 102a with bone segment 102b while simultaneously holding reduction plate 110 in place across fracture 104.

Figures 5, 6:
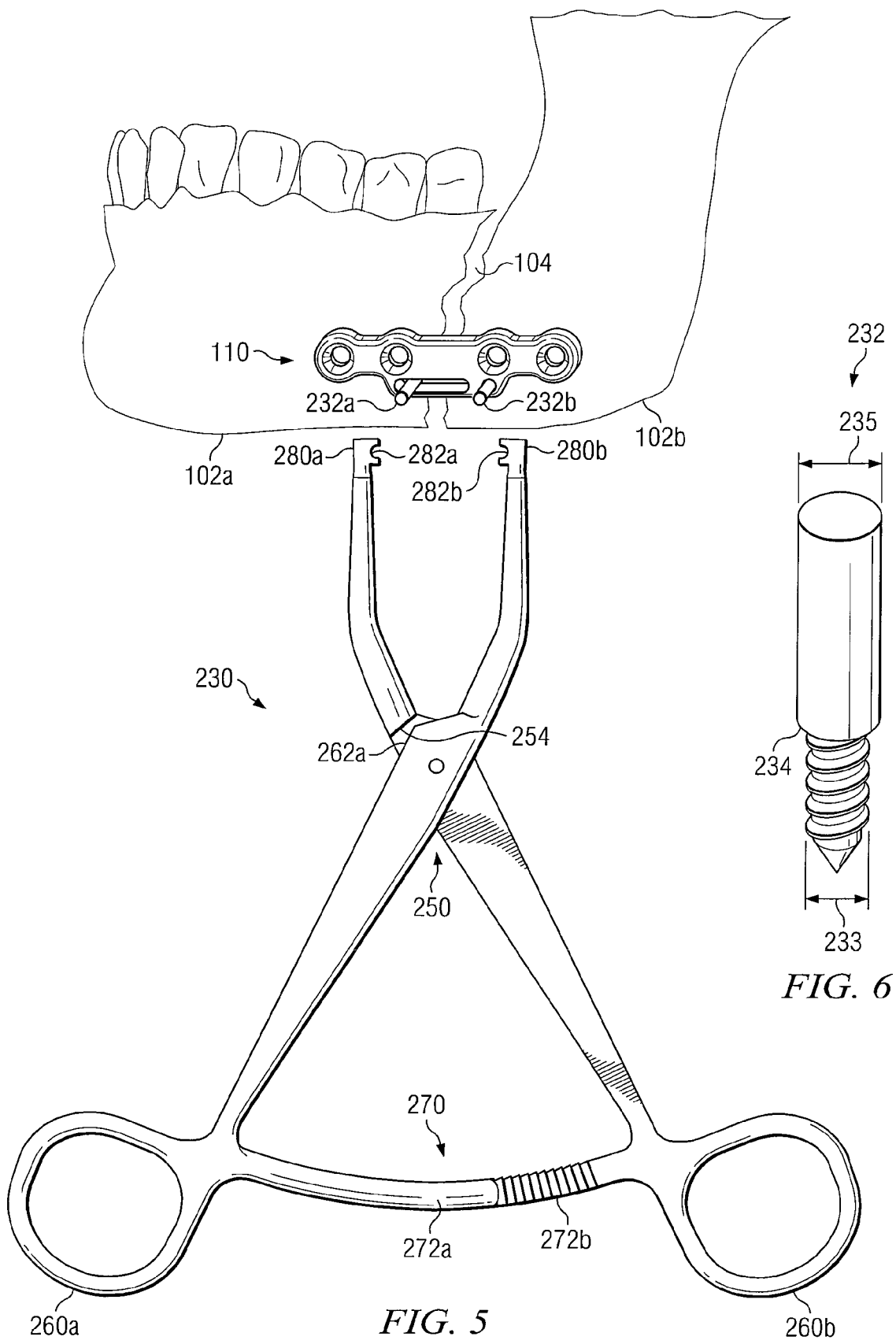
FIG. 5 illustrates an example embodiment of a system for fracture reduction wherein a forceps (including a pair of clamps) may be used to reduce a fracture by capturing a pair of pins that have been previously inserted into the fractured bone of FIG. 1 through the reduction plate of FIG. 2.
FIG. 6 illustrates an isometric view of an example embodiment of one of the pins of FIG. 5.

FIG. 5 illustrates an example embodiment of system 100 wherein a forceps 230 (including a pair of clamps 280) may be used to reduce fracture 104 by capturing a pair of pins 232 that have been previously inserted into bone segments 102a and 102b through reduction plate 110. Forceps 230 includes a first handle 260a and a second handle 260b coupled to clamps 280a and 232b through a hinge 250. Forceps 230 further includes an adjustment mechanism 270 disposed between handles 260a and 260b whereby handle 260a may be lockably positioned relative to handle 260b. In particular embodiments, one or more of the components of forceps 230 (e.g., handles 260, adjustment mechanism 270, hinge 250 and stop 254) may be structurally and/or functionally similar or identical to their counterparts in forceps 130 (e.g., described with reference to FIG. 3). As an example and not by way of limitation, stop 254 may prevent clamps 280 from opening wider than the distance between the outermost ends of travel slot 118 and anchor hole 116 (e.g., end 117 of anchor hole 116 and end 119 of travel slot 118).

To reduce fracture 104 using forceps 230 and pins 232 in an example situation, a surgeon may drill a first fastening hole 105a (NOT PICTURED) in bone segment 102a and a second fastening hole 105b (NOT PICTURED) in bone segment 102b (e.g., using either reduction plate 110 or forceps 230 as a guide to gauge an appropriate separation distance between fastening holes 105). After drilling fastening holes 105a and 105b, the surgeon may place reduction plate 110 over bone segments 102a and 102b such that anchor hole 116 aligns with fastening hole 105a and travel slot 118 aligns with fastening hole 105b. The surgeon may then insert pin 232a into bone segment 102a through anchor hole 116 and pin 232b into bone segment 102b through travel slot 118 such that pins 232 rigidly couple to bone segments 102a and 102b through reduction plate 110. Thus, pins 232 may contiguously engage anchor plate 110 and bone 102.

After inserting pins 232 into bone segments 102a and 102b through reduction plate 110, a surgeon may use forceps 230 to capture pins 232 via clamps 280. Each of clamps 280 may be any mechanical device or fixture capable of rigidly engaging pins 232 such that mechanical force may be transmitted from forceps 230 to pins 232. As an example and not by way of limitation, each of clamps 280 may include a notch 282 configured to capture one of pins 232. In particular embodiments, a radius of notch 282 may correspond to a radius of pin 232 such that pin 232 fits snugly within notch 282. Once clamps 280 have captured pins 232, forceps 230 may be used to align bone segment 102a with bone segment 102b (e.g., by squeezing bone segments 102a and 102b together).

Once bone segment 102a has been properly aligned with bone segment 102b, reduction plate 110 may be affixed to bone segments 102a and 102b using, for example, bone screws 106 such that reduction plate 110 rigidly couples bone segment 102a to bone segment 102b. After affixing reduction plate 110 to bone segments 102a and 102b, the surgeon may release forceps 230 from pins 232 and may remove pins 232 from bone 102 leaving fracture 104 to heal.

FIG. 6 illustrates an isometric view of an example embodiment of pin 232. In particular embodiments, each of pins 232 may include a shoulder 234 configured to rest on the edge of travel slot 118 or anchor hole 116 while a portion of pin 232 disposed below shoulder 234 may be configured to extend through travel slot 118 or anchor hole 116 into bone 102. For example, a diameter 233 of a portion of pin 232 disposed below shoulder 234 may be smaller in diameter than the width 126 of travel slot 118, while a diameter 235 of shoulder 234 may be greater in diameter than the width 126 of travel slot 118. Consequently, when pin 232 is inserted into travel slot 118, shoulder 234 may rest on (e.g., abut) the edge 125 of travel slot 118 while the portion of pin 232 disposed below shoulder 234 may extend through travel slot 118. As an additional example and not by way of limitation, a diameter 233 of the portion of pin 232 disposed below shoulder 234 may be smaller in diameter than the diameter of anchor hole 116, while a diameter 235 of shoulder 234 may be greater in diameter than the diameter of anchor hole 116. Consequently, when pin 232 is inserted into anchor hole 116, shoulder 234 may rest on (e.g., abut) the edge 127 of anchor hole 116 while the portion of pin 232 disposed below shoulder 234 may extend through anchor hole 116.

In particular embodiments, each of pins 232 may include a shoulder that may be used to position and hold reduction plate 110 in place over fracture 104. In particular embodiments a first pin 232a may by rigidly coupled to bone segment 102a through anchor hole 116 and a second pin 232b may be rigidly coupled to bone segment 102b through travel slot 118. In particular embodiments a surgeon may use clamps 180 to capture pins 232a and 232b and may reduce fracture 104 by closing forceps 230 using an adjustment mechanism 270. Once reduction plate 110 has been secured with at least one bone screw 106 on either side of fracture 104, forceps 230 and pins 232 may be removed, and any remaining screw holes 114 may be pilot drilled and screwed to bone 102 with bone screws 106.

One of ordinary skill in the art will appreciate that the above-described embodiments of system 100 were presented for the sake of explanatory simplicity and will further appreciate that the present disclosure contemplates inserting any suitable positioning elements (e.g., tips 132 or pins 232) into bone segments 102a and 102b through reduction plate 110 such that a suitable forceps (e.g., forceps 130 or forceps 230) may be used to lockably align bone segment 102a with bone segment 102b while holding fracture plate 110 in place over fracture 104.

Figure 7:
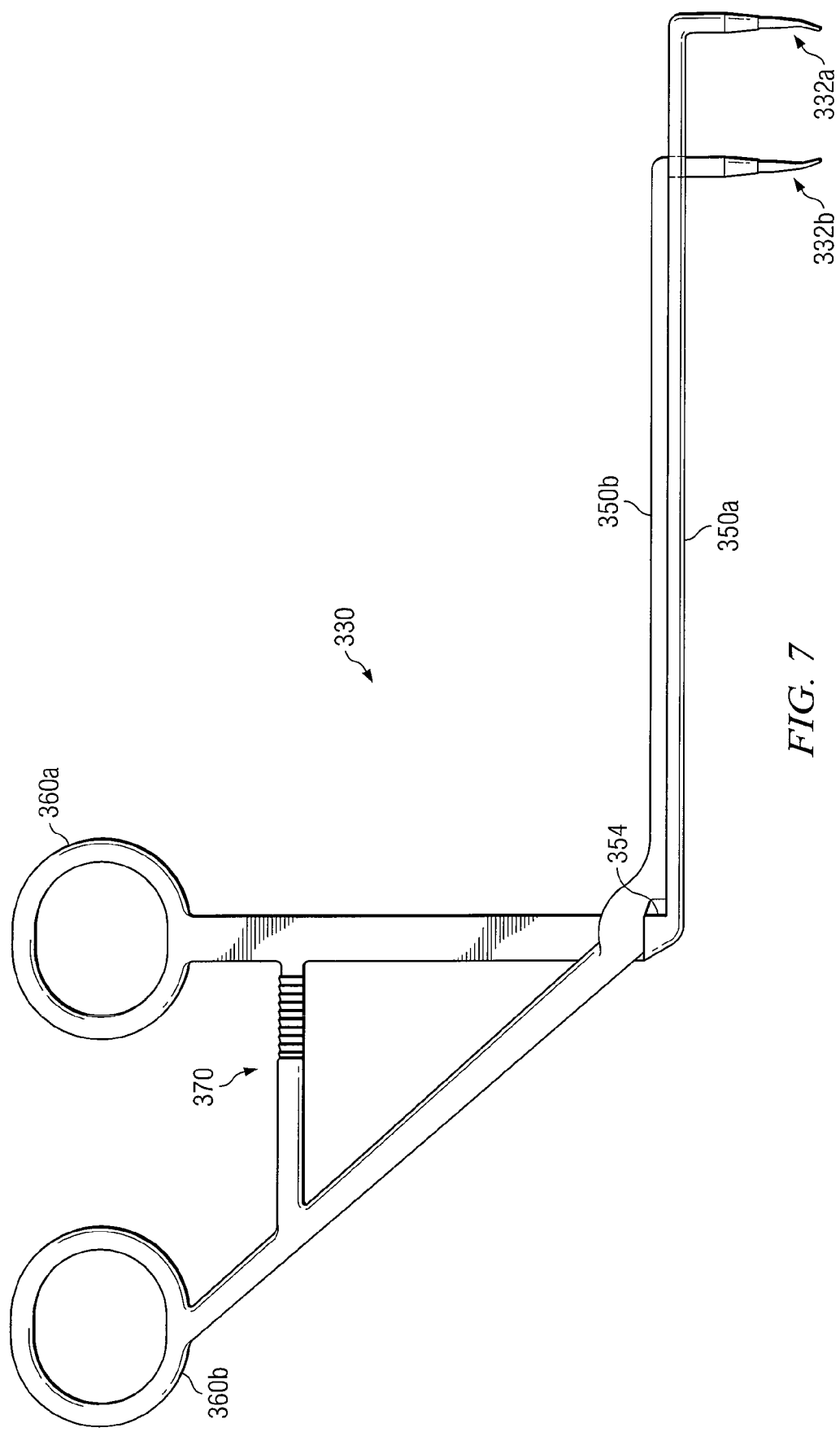
FIG. 7 illustrates an example embodiment of a slideable forceps.

FIG. 7 illustrates an example embodiment of a slideable forceps 330 that may be included in system 100. In particular embodiments, slideable forceps 330 may include either tips 332 (similar in character to tips 132) or clamps 380 (similar in character to clamps 280). Forceps 330 includes a first handle 360a and a second handle 360b coupled to tips 332a and 332b (or clamps 380a and 380b, if applicable) by a slide 350. In particular embodiments, slide 350 may comprise a top rail 350b slidably coupled to a bottom rail 350a using, for example, a dovetail and flute engagement between rails 350. Top rail 350b may be affixed to tip 332b and bottom rail 350a may be affixed to tip 332a such that a surgeon may draw tips 332 together by squeezing handles 360 together. In particular embodiments, tip 332b may extend through bottom rail 350a, for example, through a slot in bottom rail 350a. In particular embodiments, forceps 330 may further include an adjustment mechanism 370 whereby handle 360a may be lockably positioned relative to handle 360b. In particular embodiments, forceps 330 may further include a stop 354 that may limit the maximum separation distance between tips 332 to correspond to the distance between opposing ends of travel slot 118 and anchor hole 116 (or between the outermost ends of two travel slots 118, if applicable).

Although the present disclosure has been described in several embodiments, a myriad of changes, substitutions, and modifications may be suggested to one skilled in the art, and it is intended that the present disclosure encompass such changes, substitutions, and modifications as fall within the scope of the present appended claims.

What is claimed is:

1. A system for fracture reduction, comprising:
a reduction plate for reducing a fracture between a first bone segment and a second bone segment, the reduction plate comprising:
on a first side of the reduction plate, a travel slot and a first screw hole wherein the travel slot is configured to slidably engage a first positioning element that extends into the first bone segment through the travel slot and the first screw hole is configured to affix the first side of the reduction plate to the first bone segment via a first bone screw; and
on a second side of the reduction plate, an adjustment hole and a second screw hole wherein the adjustment hole is configured to engage a second positioning element that extends into the second bone segment through the adjustment hole and the second screw hole is configured to affix the second side of the reduction plate to the second bone segment via a second bone screw; and
a forceps, the forceps comprising a first tip and a second tip respectively coupled to a first handle and a second handle via a hinge wherein the forceps comprises a stop that limits a maximum separation distance between the first tip and the second tip, the maximum separation distance corresponding to a distance between a first end of the travel slot and an opposing end of the adjustment hole.

2. The system of claim 1, wherein:
the first positioning element is the first tip of the forceps and the second positioning element is the second tip of the forceps; and
once the first tip is inserted into the first bone segment through the travel slot and the second tip is inserted into the second bone segment through the adjustment hole, the forceps are operable to adjust a width of the fracture while holding the first side of the reduction plate over the first bone segment and the second side of the reduction plate over the second bone segment.

3. The system of claim 1, wherein the first positioning element and the second positioning element respectively comprise a first shoulder and a second shoulder, the first shoulder configured to rest on a first edge of the travel slot and the second shoulder configured to rest on a second edge of the adjustment hole; and
a portion of the first positioning element disposed below the first shoulder comprises a diameter that is less than a width of the travel slot and the first shoulder comprises a diameter that is greater than the width of the travel slot.

4. The system of claim 1, wherein the first tip and the second tip are tapered such that the first tip is operable to capture the reduction plate by wedging into the travel slot and the second tip is operable to capture the reduction plate by wedging into the adjustment hole.

5. The system of claim 2, wherein:
a first end of the first tip and a second end of the second tip are hooked inward such that the first end and the second end point toward one another;
the first tip and the second tip are bent at an angle such that the first tip and the second tip are angled up or down relative to a plane including the first handle and the second handle; and
the forceps comprise an adjustment mechanism operable to lockably adjust a separation distance between the first tip and the second tip.

6. The system of claim 1, further comprising a first pin a second pin, wherein:
the first positioning element is the first pin and the second positioning element is the second pin;
the first tip is configured to rigidly engage the first pin the and the second tip is configured to rigidly engage the second pin; and
once the first pin and the second pin are inserted through the reduction plate respectively into the first bone segment and the second bone segment and the first tip engages the first pin and the second tip engages the second pin, the forceps are operable to adjust a width of the fracture while holding the first side of the reduction plate over the first bone segment and the second side of the reduction plate over the second bone segment.

7. The system of claim 1, wherein the adjustment hole comprises a second travel slot configured to slidably engage the second positioning element.

8. The system of claim 1, wherein the adjustment hole comprises an anchor hole configured to rigidly engage the second positioning element.

9. The system of claim 1, wherein the first screw hole and the second screw hole are aligned along a first axis while the travel slot and the adjustment hole are aligned along a second axis wherein the first axis is different from the second axis.

10. The system of claim 1, wherein:
the first tip and the second tip are respectively coupled to the first handle and the second handle via a slide;
the first positioning element is the first tip of the forceps and the second positioning element is the second tip of the forceps; and
once the first tip is inserted into the first bone segment through the travel slot and the second tip is inserted into the second bone segment through the adjustment hole, the slideable forceps are operable to adjust a width of the fracture while holding the first side of the reduction plate over the first bone segment and the second side of the reduction plate over the second bone segment.

11. A method for forming a system for fracture reduction, comprising:
forming a reduction plate for reducing a fracture between a first bone segment and a second bone segment, the reduction plate comprising:
on a first side of the reduction plate, a travel slot and a first screw hole wherein the travel slot is configured to slidably engage a first positioning element that extends into the first bone segment through the travel slot and the first screw hole is configured to affix the first side of the reduction plate to the first bone segment via a first bone screw; and
on a second side of the reduction plate, an adjustment hole and a second screw hole wherein the adjustment hole is configured to engage a second positioning element that extends into the second bone segment through the adjustment hole and the second screw hole is configured to affix the second side of the reduction plate to the second bone segment via a second bone screw; and
forming a forceps, the forceps comprising a first tip and a second tip respectively coupled to a first handle and a second handle via a hinge wherein the forceps comprises a stop that limits a maximum separation distance between the first tip and the second tip, the maximum separation distance corresponding to a distance between a first end of the travel slot and an opposing end of the adjustment hole.

12. The method of claim 11, wherein:
the first tip and the second tip respectively comprise the first positioning element and the second positioning element; and
once the first tip is inserted into the first bone segment through the travel slot and the second tip is inserted into the second bone segment through the adjustment hole, the forceps are operable to adjust a width of the fracture while holding the first side of the reduction plate over the first bone segment and the second side of the reduction plate over the second bone segment.

13. The method of claim 11, wherein the first positioning element and the second positioning element respectively comprise a first shoulder and a second shoulder, the first shoulder configured to rest on a first edge of the travel slot and the second shoulder configured to rest on a second edge of the adjustment hole; and
a portion of the first positioning element disposed below the first shoulder comprises a diameter that is less than a width of the travel slot and the first shoulder comprises a diameter that is greater than the width of the travel slot.

14. The method of claim 11, wherein the first tip and the second tip are tapered such that the first tip is operable to capture the reduction plate by wedging into the travel slot and the second tip is operable to capture the reduction plate by wedging into the adjustment hole.

15. The method of claim 12, wherein:
a first end of the first tip and a second end of the second tip are hooked inward such that the first end and the second end point toward one another;
the first tip and the second tip are bent at an angle such that the first tip and the second tip are angled up or down relative to a plane including the first handle and the second handle; and
the forceps comprise an adjustment mechanism operable to lockably adjust a separation distance between the first tip and the second tip.

16. The method of claim 11, comprising forming a first pin, a second pin a second pin, wherein:
the first positioning element is the first pin and the second positioning element is the second pin;
the first tip is configured to rigidly engage the first pin the and the second tip is configured to rigidly engage the second pin; and
once the first pin and the second pin are inserted through the reduction plate respectively into the first bone segment and the second bone segment and the first tip engages the first pin and the second tip engages the second pin, the forceps are operable to adjust a width of the fracture while holding the first side of the reduction plate over the first bone segment and the second side of the reduction plate over the second bone segment.

17. The method of claim 11, wherein the adjustment hole comprises a second travel slot configured to slidably engage the second positioning element.

18. The method of claim 11, wherein the adjustment hole comprises an anchor hole configured to rigidly engage the second positioning element.

19. The method of claim 11, wherein the first screw hole and the second screw hole are aligned along a first axis while the travel slot and the adjustment hole are aligned along a second axis wherein the first axis is different from the second axis.

20. A method for fracture reduction, comprising:
using a reduction plate to reduce a fracture between a first bone segment and a second bone segment, the reduction plate comprising:

on a first side of the reduction plate, a travel slot and a first screw hole wherein the travel slot is configured to slidably engage a first positioning element that extends into the first bone segment through the travel slot and the first screw hole is configured to affix the first side of the reduction plate to the first bone segment via a first bone screw; and on a second side of the reduction plate, an adjustment hole and a second screw hole wherein the adjustment hole is configured to engage a second positioning element that extends into the second bone segment through the adjustment hole and the second screw hole is configured to affix the second side of the reduction plate to the second bone segment via a second bone screw; and using a forceps in conjunction with the reduction plate to reduce a fracture, the forceps comprising a first tip and a second tip respectively coupled to a first handle and a second handle via a hinge wherein the forceps comprises a stop that limits a maximum separation distance between the first tip and the second tip, the maximum separation distance corresponding to a distance between a first end of the travel slot and an opposing end of the adjustment hole.

21. The method of claim 20, wherein the first tip and the second tip respectively comprise the first positioning element and the second positioning element, and further comprising:

inserting the first tip into the first bone segment through the travel slot and the second tip into the second bone segment through the adjustment hole; and using the forceps to adjust a width of the fracture while holding the first side of the reduction plate over the first bone segment and the second side of the reduction plate over the second bone segment.

22. The method of claim 20, wherein:

the first positioning element and the second positioning element respectively comprise a first shoulder and a second shoulder, the first shoulder configured to rest on a first edge of the travel slot and the second shoulder configured to rest on a second edge of the adjustment hole; and a portion of the first positioning element disposed below the first shoulder comprises a diameter that is less than a width of the travel slot and the first shoulder comprises a diameter that is greater than the width of the travel slot.

23. The method of claim 21, wherein:

a first end of the first tip and a second end of the second tip are hooked inward such that the first end and the second end point toward one another;

the first tip and the second tip are bent at an angle such that the first tip and the second tip are angled up or down relative to a plane including the first handle and the second handle; and the forceps comprise an adjustment mechanism operable to lockably adjust a separation distance between the first tip and the second tip.

24. The method of claim 20, wherein the first positioning element is a first pin and the second positioning element is a second pin, and further comprising:

using a forceps in conjunction with the reduction plate, the first pin, and the second pin to reduce the fracture, the forceps comprising a first clamp and a second clamp respectively coupled to a first handle and a second handle via a hinge wherein the forceps comprises a stop that limits a maximum separation distance between the first clamp and the second clamp, the maximum separation distance corresponding to a distance between a first end of the travel slot and an opposing end of the adjustment hole;

inserting the first pin and the second pin through the reduction plate respectively into the first bone segment and the second bone segment;

rigidly engaging the first clamp with the first pin the and the second clamp with the second pin; and using the forceps to adjust a width of the fracture while holding the first side of the reduction plate over the first bone segment and the second side of the reduction plate over the second bone segment.

* * * * *